United States Patent
Lovchik et al.

(10) Patent No.: US 10,800,722 B2
(45) Date of Patent: Oct. 13, 2020

(54) 6-ISOPROPYL-2,4-DIMETHYLCYCLOHEXEN-1-OL COMPOUNDS AS FRAGRANCE INGREDIENTS

(71) Applicant: Givaudan SA, Vernier (CH)

(72) Inventors: Martin Alan Lovchik, Dübendorf (CH); Veronika Zelenay, Kemptthal (CH)

(73) Assignee: Givaudan S. A., Vernier (CH)

( * ) Notice: Subject to any disclaimer, the term of this patent is extended or adjusted under 35 U.S.C. 154(b) by 0 days.

(21) Appl. No.: 16/318,171

(22) PCT Filed: Jul. 27, 2017

(86) PCT No.: PCT/EP2017/068999
§ 371 (c)(1),
(2) Date: Jan. 16, 2019

(87) PCT Pub. No.: WO2018/019935
PCT Pub. Date: Feb. 1, 2018

(65) Prior Publication Data
US 2019/0233357 A1    Aug. 1, 2019

(30) Foreign Application Priority Data
Jul. 27, 2016    (GB) .................................. 1613013.0

(51) Int. Cl.
| | | |
|---|---|---|
| *C07C 35/18* | (2006.01) | |
| *C11B 9/00* | (2006.01) | |
| *A61Q 13/00* | (2006.01) | |
| *A61K 8/34* | (2006.01) | |
| *A61Q 19/10* | (2006.01) | |

(52) U.S. Cl.
CPC ................ *C07C 35/18* (2013.01); *A61K 8/34* (2013.01); *A61Q 13/00* (2013.01); *A61Q 19/10* (2013.01); *C11B 9/0015* (2013.01); *C11B 9/0034* (2013.01); *C07C 2601/16* (2017.05)

(58) Field of Classification Search
CPC ..... C07C 35/18; C07C 2601/16; A61Q 19/10; A61Q 13/00; A61K 8/34; C11B 9/0015; C11B 9/0034
See application file for complete search history.

(56) References Cited

U.S. PATENT DOCUMENTS

| | | |
|---|---|---|
| 4,326,997 A | 4/1982 | Willis et al. |
| 5,268,356 A | 12/1993 | Decorzant et al. |
| 2011/0281949 A1 | 11/2011 | Minke et al. |
| 2013/0123548 A1 | 5/2013 | Muratore et al. |
| 2015/0376103 A1 | 12/2015 | Chanot et al. |
| 2017/0174602 A1 | 6/2017 | Chanot et al. |

FOREIGN PATENT DOCUMENTS

| | | |
|---|---|---|
| WO | WO 01/00551 A1 | 1/2001 |
| WO | WO 2010/015965 A2 | 2/2010 |
| WO | WO 2014/053744 A1 | 4/2014 |
| WO | WO 2016/149567 A1 | 9/2016 |

OTHER PUBLICATIONS

PCT/EP2017/068999—International Search Report, dated Nov. 8, 2017.
PCT/EP2017/068999—International Written Opinion, dated Nov. 8, 2017.

*Primary Examiner* — Rosalynd A Keys
(74) *Attorney, Agent, or Firm* — Curatolo Sidoti Co., LPA; Salvatore A. Sidoti; Floyd Trillis, III

(57) ABSTRACT

The present invention refers to 6-isopropyl-2,4-dimethylcyclohexen-1-ol derivatives, to a method of their production, and fragrance compositions and fragranced articles comprising them.

8 Claims, No Drawings

6-ISOPROPYL-2,4-DIMETHYLCYCLOHEXEN-1-OL COMPOUNDS AS FRAGRANCE INGREDIENTS

CROSS REFERENCE TO RELATED APPLICATIONS

This application is a national stage application of International Application No. PCT/EP2017/068999, filed 27 Jul. 2017, which claims priority from Great Britain Patent Application No. 1613013.0, filed 27 Jul. 2016, which applications are incorporated herein by reference.

The present invention relates to 6-isopropyl-2,4-dimethylcyclohexen-1-ol derivatives having green, very impactful odor notes, and to their use as flavor and fragrance ingredient and to compositions and products comprising them. It furthermore relates to a method of their production.

Green odor characteristics are important scents in perfumery. Albeit a wide range of compounds possessing green odor notes are known, there is a constant demand for new compounds that enhance, modify or improve on odor notes.

It has now been found that certain 6-isopropyl-2,4-dimethylcyclohexen-1-ol derivatives posse a very impactful green odor notes.

Accordingly, in a first aspect there is provided the use as flavor or fragrance a compound of formula (I)

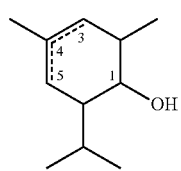

(I)

wherein the bond between C-3 and C-4 together with dotted line represents a single bond and the bond between C-4 and C-5 together with the dotted line represents a double bond; or
the bond between C-3 and C-4 together with dotted line represents a double bond and the bond between C-4 and C-5 together with the dotted line represents a single bond.

The compounds of formula (I) as defined hereinabove contains three stereocenters, and as such exist as mixtures of stereoisomers. They can be used as stereoisomeric mixtures, or may be resolved in diasteromerically and/or enantiomerically pure form. Resolving stereoisomers adds to the complexity of manufacture and purification of these compounds, and so it is preferred to use the compounds as mixtures of their stereoisomers simply for economic reasons. However, if it is desired to prepare individual stereoisomers, this may be achieved according to methodology known in the art, e. g. preparative HPLC and GC or by stereoselective syntheses.

As a specific example of compounds of formula (I) one may cite 6-isopropyl-2,4-dimethylcyclohex-3-en-1-ol, which exist in four pairs of enantiomers, namely, rel-(1R, 2S, 6S)-6-isopropyl-2,4-dimethylcyclohex-3-en-1-ol;
rel-(1R, 2S, 6R)-6-isopropyl-2,4-dimethylcyclohex-3-en-1-ol;
rel-(1R, 2R, 6S)-6-isopropyl-2,4-dimethylcyclohex-3-en-1-ol; and
rel-(1R, 2R, 6R)-6-isopropyl-2,4-dimethylcyclohex-3-en-1-ol, each of which forms part of the invention.

Whereas all diasteromers of 6-isopropyl-2,4-dimethylcyclohex-3-en-1-ol possess a green, rooty, earthy, pyrazin-like odor notes, it was observed that in particular rel-(1R, 2S, 6S)-6-isopropyl-2,4-dimethylcyclohex-3-en-1-ol possess a very impactful odor profile.

As a further example of compounds of formula (I) one may cite 6-isopropyl-2,4-dimethylcyclohex-4-en-1-ol.

The compound of formula (I) may be used alone, as stereoisomeric mixture, or in combination with a base material. As used herein, the 'base material' includes all known odorant molecules selected from the extensive range of natural products, and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art.

The term "auxiliary agent" refers to ingredients that might be employed in a fragrance composition for reasons not specifically related to the olfactive performance of said composition. For example, an auxiliary agent may be an ingredient that acts as an aid to processing a fragrance ingredient or ingredients, or a composition containing said ingredient(s), or it may improve handling or storage of a fragrance ingredient or composition containing same. It might also be an ingredient that provides additional benefits such as imparting color or texture. It might also be an ingredient that imparts light resistance or chemical stability to one or more ingredients contained in a fragrance composition. A detailed description of the nature and type of adjuvants commonly used in fragrance compositions containing same cannot be exhaustive, but it has to be mentioned that said ingredients are well known to a person skilled in the art.

As used herein, 'fragrance composition' means any composition comprising the compound of formula (I) and a base material, e.g. a diluent conventionally used in conjunction with odorants, such as diethyl phthalate (DEP), dipropylene glycol (DPG), isopropyl myristate (IPM), triethyl citrate (TEC) and alcohol (e.g. ethanol). Optionally, the composition may comprise an anti-oxidant adjuvant. Said anti-oxidant may be selected from Tinogard® TT (BASF), Tinogard® Q (BASF), Tocopherol (including its isomers, CAS 59-02-9; 364-49-8; 18920-62-2; 121854-78-2), 2,6-bis (1,1-dimethylethyl)-4-methylphenol (BHT, CAS 128-37-0) and related phenols, hydroquinones (CAS 121-31-9).

The following list comprises examples of known odorant molecules, which may be combined with the compound of the present invention:

essential oils and extracts, e.g. castoreum, costus root oil, oak moss absolute, geranium oil, tree moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil and/or ylang-ylang oil;

alcohols, e.g. cinnamic alcohol ((E)-3-phenylprop-2-en-1-ol); cis-3-hexenol ((Z)-hex-3-en-1-ol); citronellol (3,7-dimethyloct-6-en-1-ol); dihydro myrcenol (2,6-dimethyloct-7-en-2-ol); Ebanol™ ((E)-3-methyl-5-(2,2,3-trimethylcyclopent-3-en-1-yl)pent-4-en-2-ol); eugenol (4-allyl-2-methoxyphenol); ethyl linalool ((E)-3,7-dimethylnona-1,6-dien-3-ol); farnesol ((2E,6Z)-3,7,11-trimethyldodeca-2,6,10-trien-1-ol); geraniol ((E)-3,7- dimethylocta-2,6-dien-1-ol); Super Muguet™ ((E)-6-ethyl-3-methyloct-6-en-1-ol); linalool (3,7-dimethylocta-1,6-dien-3-ol); menthol (2-isopropyl-5-methylcyclohexanol); Nerol (3,7-dimethyl-2,6-octadien-1-ol); phenyl ethyl alcohol (2-phenylethanol); Rhodinol™ (3,7-dimethyloct-6-en-1-ol); Sandalore™ (3-methyl-5-(2,2,3-trimethylcyclopent-3-en-1-yl)pentan-2-ol); terpineol (2-(4-methylcyclohex-3-en-1-yl)propan-2-ol); or Timberol™ (1-(2,2,6-trimethylcyclohexyl)hexan-3-ol); 2,4,7-trimethylocta-2,6-dien-1-ol, and/or [1-methyl-2(5-methylhex-4-en-2-yl)cyclopropyl]-methanol;

aldehydes and ketones, e.g. anisaldehyde (4-methoxybenzaldehyde); alpha amyl cinnamic aldehyde (2-benzylideneheptanal); Georgywood™ (1-(1,2,8,8-tetramethyl-1,2,3,4,5,6,7,8-octahydronaphthalen-2-yl)ethanone); Hydroxycitronellal (7-hydroxy-3,7-dimethyloctanal); Iso E Super® (1-(2,3,8,8-tetramethyl-1,2,3,4,5,6,7,8-octahydronaphthalen-2-yl)ethanone); Isoraldeine® ((E)-3-methyl-4-(2,6,6-trimethylcyclohex-2-en-1-yl)but-3-en-2-one); Hedione® (methyl 3-oxo-2-pentylcyclopentaneacetate); 3-(4-isobutyl-2-methylphenyl)propanal; maltol; methyl cedryl ketone; methylionone; verbenone; and/or vanillin;

ether and acetals, e.g. Ambrox® (3a,6,6,9a-tetramethyl-2,4,5,5a,7,8,9,9b-octahydro-1H-benzo[e][1]benzofuran); geranyl methyl ether ((2E)-1-methoxy-3,7-dimethylocta-2,6-diene); rose oxide (4-methyl-2-(2-methylprop-1-en-1-yl)tetrahydro-2H-pyran); bis((3-methylbut-2-en-1-yl)oxy)methane and/or Spirambrene® (2',2',3,7,7-pentamethylspiro[bicyclo[4.1.0]heptane-2,5'-[1,3]dioxane]);

esters and lactones, e.g. benzyl acetate; cedryl acetate ((1S,6R,8aR)-1,4,4,6-tetramethyloctahydro-1H-5,8a-methanoazulen-6-yl acetate); γ-decalactone (6-pentyltetrahydro-2H-pyran-2-one); Helvetolide® (2-(1-(3,3-dimethylcyclohexyl)ethoxy)-2-methylpropyl propionate); γ-undecalactone (5-heptyloxolan-2-one); and/or vetiveryl acetate ((4,8-dimethyl-2-propan-2-ylidene-3,3a,4,5,6,8a-hexahydro-1H-azulen-6-yl) acetate);

macrocycles, e.g. Ambrettolide ((Z)-oxacycloheptadec-10-en-2-one); ethylene brassylate (1,4-dioxacycloheptadecane-5,17-dione); and/or Exaltolide® (16-oxacyclohexadecan-1-one); and heterocycles, e.g. isobutylquinoline (2-isobutylquinoline).

Further examples of known fragrance ingredients with which 2,4,7-trimethyloct-6-en-1-ol may be combined include 6-methoxy-2,6-dimethylheptan-1-al (Methoxymelonal); 5,9-dimethyl-4,8-decadienal (Geraldehyde); octahydro-8,8-dimethylnaphthalene-2-carbaldehyde (Cyclomyral); 5-methyl-2-(1-methylbutyl)-5-propyl-1,3-dioxan (Troenan); 3,7,11-trimethyldodeca-1,6,10-trien-3-ol (optionally as an isomeric mixture) (Nerolidol); 2-methyl-4-phenylbutan-2-ol (dimethylphenylethylcarbinol); 1-(1-hydroxyethyl)-4-(1-methylethyl)cyclohexane (optionally as a mixture of the diastereoisomers) (Mugetanol); (4-methyl-3-pentenyl)cyclohexenecarbaldehyde (Citrusal); 3-(p-(2-methylpropyl)phenyl)-2-methylpropionaldehyde (Silvial); 3-p-cumenyl-2-methylpropionaldehyde (Cyclamenaldehyde); and mixtures of: cis-tetrahydro-2-isobutyl-4-methylpyran-4-ol and trans-tetrahydro-2-isobutyl-4-methylpyran-4-ol.

Even further examples of known fragrance ingredients may include Amyl Salicylate (pentyl 2-hydroxybenzoate); Aurantiol® ((E)-methyl 2-((7-hydroxy-3,7-dimethyloctylidene)amino)benzoate); Benzyl Salicylate (benzyl 2-hydroxybenzoate); Cis-3-hexenyl Salicylate ((Z)-hex-3-en-1-yl 2-hydroxybenzoate); Citronellyl Oxyacetaldehyde (2-((3,7-dimethyloct-6-en-1-yl)oxy)acetaldehyde); Cyclemax (3-(4-propan-2-ylphenyl)propanal); Cyclohexyl Salicylate (cyclohexyl 2-hydroxybenzoate); Cyclomyral® (8,8-dimethyl-1,2,3,4,5,6,7,8-octahydronaphthalene-2-carbaldehyde); Cyclopentol (2-pentylcyclopentan-1-ol); Cymal (4-(4-hydroxy-4-methylpentyl)cyclohex-3-enecarbaldehyde); Dupical ((E)-4-((3aS,7aS)-hexahydro-1H-4,7-methanoinden-5(6H)-ylidene)butanal); Floral Super ((4E)-4,8-dimethyldeca-4,9-dienal); Florhydral® (3-(3-isopropylphenyl)butanal); Florol® (2-isobutyl-4-methyltetrahydro-2H-pyran-4-ol); Gyrane (2-butyl-4,6-dimethyl-3,6-dihydro-2H-pyran); Hexyl Salicylate (hexyl 2-hydroxybenzoate); Helional (3-(1,3-benzodioxol-5-yl)-2-methylpropanal); Lyral® (4-(4-hydroxy-4-methylpentyl)cyclohex-3-enecarbaldehyde); Majantol® (2,2-dimethyl-3-(m-tolyl)propan-1-ol); Mayol® ((4-isopropylcyclohexyl)-methanol); Melafleur (8,8-dimethyl-2,3,4,5,6,7-hexahydro-1H-naphthalene-2-carbaldehyde); Melonal (2,6-dimethylhept-5-enal); Muguesia (3-methyl-4-phenylbutan-2-ol); Muguet alcohol (3-cyclohexyl-2,2-dimethylpropan-1-ol); Verdantiol ((E)-methyl 2-((3-(4-(tert-butyl)phenyl)-2-methylprop-1-en-1-yl)amino) benzoate); Peonile (2-cyclohexylidene-2-phenylacetonitrile); Phenoxanol® (3-methyl-5-phenylpentan-1-ol); Rossitol® (3-isobutyl-1-methylcyclohexanol); Suzaral (2-methyl-3-[4-(2-methylpropyl)phenyl]propanal); Muguol® (3,7-dimethylocta-4,6-dien-3-ol); Tetrahydro Linalool (3,7-dimethyloctan-3-ol); Acalea ((2E)-2-[(4-methylphenyl)methylidene]-heptanal); Dihydro IsoJasmonate (methyl 2-hexyl-3-oxocyclopentane-1-carboxylate); Hexyl Cinnamic Aldehyde ((E)-2-benzylideneoctanal); Acetoin (3-hydroxybutan-2-one); Adoxal (2,6,10-trimethylundec-9-enal); Aldolone® (7-propyl-2H-1,5-benzodioxepin-3(4H)-one); Ambrocenide® ((4aR,5R,7aS,9R)-Octahydro-2,2,5,8,8,9a-hexamethyl-4H-4a,9-methanoazuleno[5,6-d]-1,3-dioxole); Ambroxan (3a,6,6,9a-tetramethyl-2,4,5,5a,7,8,9,9b-octahydro-1H-benzo[e][1]benzofuran); Bacdanol® ((E)-2-ethyl-4-(2,2,3-trimethylcyclopent-3-en-1-yl)but-2-en-1-ol); Calone 1951® (7-methyl-2H-benzo[b][1,4]dioxepin-3(4H)-one); Cetalox® (3a,6,6,9a-tetramethyl-2,4,5,5a,7,8,9,9b-octahydro-1H-benzo[e][1]benzofuran); Cinnamic alcohol ((E)-3-phenylprop-2-en-1-ol); Citral ((E)-3,7-dimethylocta-2,6-dienal); Cyclabute ((3aR,6S,7aS)-3a,4,5,6,7,7a-hexahydro-1H-4,7-methanoinden-6-ylisobutyrate); Cyclacet™ ((3aR,6S,7aS)-3a,4,5,6,7,7a-hexahydro-1H-4,7-methanoinden-6-yl acetate); Cyclaprop ((3aR,6S,7aS)-3a,4,5,6,7,7a-hexahydro-1H-4,7-methanoinden-6-yl propionate); Cyclohexadecanolide; Cyclohexadecenone; Cyclopentadecanone; Delta Damascone ((E)-1-(2,6,6-trimethylcyclohex-3-en-1-yl)but-2-en-1-one); Elintaal Forte (3-(1-ethoxyethoxy)-3,7-dimethylocta-1,6-diene); Ethyl Vanillin (3-ethoxy-4-hydroxybenzaldehyde); Exaltenone ((4Z)-cyclopentadec-4-en-1-one); Floralozone (3-(4-ethylphenyl)-2,2-dimethylpropanal); Fructalate (diethyl cyclohexane-1,4-dicarboxylate); Habanolide ((E)-oxacyclohexadec-12-en-2-one); Galaxolide (4,6,6,7,8,8-hexamethyl-1,3,4,6,7,8-hexahydro-cyclopenta[g]isochromene); Hydroxyambran® (2-cyclododecylpropan-1-ol); Myraldene (4-(4-methylpent-3-en-1-yl)cyclohex-3-enecarbaldehyde); Jasmal (3-pentyltetrahydro-2H-pyran-4-yl acetate); Javanol® ((1-methyl-2-((1,2,2-trimethylbicyclo[3.1.0]hexan-3-yl)methyl) cyclopropyl)methanol); Lauric Aldehyde (Dodecanal); Mefranal (3-methyl-5-phenylpentanal); Muscenone ((Z)-3-methylcyclopentadec-5-enone); Tonalid® (1-(3,5,5,6,8,8- hexamethyl-5,6,7,8-tetrahydronaphthalen-2-yl)ethanone); Nectaryl® (2-(2-(4-methylcyclohex-3-en-1-yl)propyl)cyclopentanone); Norlimbanol (1-(2,2,6-trimethylcyclohexyl) hexan-3-ol); Raspberry ketone (4-(4-hydroxyphenyl)butan-2-one); Pinoacetaldehyde (3-(6,6-dimethylbicyclo[3.1.1] hept-2-en-2-yl)propanal); Romandolide® (acetic acid (1-oxopropoxy)-, 1-(3,3-dimethyl cyclohexyl)ethyl ester); Sanjinol ((E)-2-ethyl-4-(2,2,3-trimethylcyclopent-3-en-1-yl)but-2-en-1-ol); and/or Velvione® ((Z)-cyclohexadec-5-enone).

A fragrance composition need not be limited to the fragrance ingredients listed above. Other fragrance ingredients commonly used in perfumery may be employed, for example any of those ingredients described in "Perfume and Flavour Chemicals", S. Arctander, Allured Publishing Corporation, 1994, IL, USA, which is incorporated herein by reference, including essential oils, plant extracts, absolutes, resinoids, odorants obtained from natural products and the like.

In one particular embodiment, compounds of formula (I) as hereinabove defined, e.g. 6-isopropyl-2,4-dimethylcyclohex-3-en-1-ol, may be combined with other alcohols, such as (E)/(Z)-2,4,7-trimethyloct-6-en-1-ol, (E)/(Z)-2,4,7-trimethylocta-2,6-dien-1-ol, (E)/(Z)-2,4,7-trimethylocta-3,6-dien-1-ol, 2,4,7-trimethyloctan-1-ol (odor description: floral, green, rosy), dihydromyrcenol, linalool, and ethyl linalool, and mixtures thereof.

In a further embodiment, this combination of formula (I) compounds with other alcohols may additionally be combined with other ingredients possessing a green odor characteristics, such as bis((3-methylbut-2-en-1-yl)oxy)methane.

The compound according to formula (I) may be used in a broad range of fragranced articles, e.g. in any field of fine and functional perfumery, such as perfume, Eau de Parfum, Eau de Cologne, Eau de Toilette, air care products, household products, laundry and fabric care products, body care products and cosmetics. The compounds can be employed in widely varying amounts, depending upon the specific application and on the nature and quantity of other fragrance ingredients. The proportion is typically from 0.00001 to 30 (including, e.g. 0.001, 0.001, 0.01, 0.1, 0.5, 0.75, 1, 2, 5, 10, 15, 20, 25) weight percent of the article. In one embodiment, the compound of the present invention may be employed in a fabric softener in an amount from 0.0001 to 0.3 weight percent. In another embodiment, the compound of the present invention may be used in fine perfumery in amounts from 0.001 to 30 weight percent (e.g. up to about 10 or up to 20 weight percent), more preferably between 0.01 and 5 weight percent. However, these values are given only by way of example, since the experienced perfumer may also achieve effects or may create novel accords with lower or higher concentrations.

The compounds of formula (I) as described hereinabove may be employed in a consumer product base simply by directly mixing the compound of formula (I), or a fragrance composition with the consumer product base, or it may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or it may be chemically bonded to substrates, which are adapted to release the fragrance molecule upon application of an external stimulus such as light, enzyme, oxygen, or the like, and then mixed with the consumer product base.

Thus, the invention additionally provides a method of manufacturing a fragranced article, comprising the incorporation of a compound of formula (I), as a fragrance ingredient, either by directly admixing the compound to the consumer product base or by admixing a fragrance composition comprising the compound of formula (I), which may then be mixed with a consumer product base, using conventional techniques and methods. Through the addition of an olfactory acceptable amount of the compound of the present invention as hereinabove described the odor notes of a consumer product base will be improved, enhanced, or modified.

Thus, the invention furthermore provides a method for improving, enhancing or modifying a consumer product base by means of the addition thereto of an olfactorily acceptable amount of the compound of formula (I).

The invention also provides a fragranced article comprising:

a) as odorant the compound of formula (I), or a mixture thereof; and b) a consumer product base.

As used herein, 'consumer product base' means a composition for use as a consumer product to fulfil specific actions, such as cleaning, softening, and caring or the like. Examples of such products include fine perfumery, e.g. perfume and eau de toilette; fabric care, household products and personal care products such as cosmetics, laundry care detergents, rinse conditioner, personal cleansing composition, detergent for dishwasher, surface cleaner; laundry products, e.g. softener, bleach, detergent; body-care products, e.g. shampoo, shower gel; air care products (includes products that contain preferably volatile and usually pleasant-smelling compounds which advantageously can even in very small amounts mask unpleasant odors). Air fresheners for living areas contain, in particular, natural and synthetic essential oils such as pine needle oils, citrus oil, eucalyptus oil, lavender oil, and the like, in amounts for example of up to 50% by weight. As aerosols they tend to contain smaller amounts of such essential oils, by way of example less than 5% or less than 2% by weight, but additionally include compounds such as acetaldehyde (in particular, <0.5% by weight), isopropyl alcohol (in particular, <5% by weight), mineral oil (in particular, <5% by weight), and propellants.

Cosmetic products include:

(a) cosmetic skincare products, especially bath products, skin washing and cleansing products, skincare products, eye makeup, lip care products, nail care products, intimate care products, foot care products;

(b) cosmetic products with specific effects, especially sunscreens, tanning products, de-pigmenting products, deodorants, antiperspirants, hair removers, and shaving products;

(c) cosmetic dental-care products, especially dental and oral care products, tooth care products, cleaners for dental prostheses, adhesives for dental prostheses; and (d) cosmetic hair care products, especially hair shampoos, hair care products, hair setting products, hair-shaping products, and hair coloring products.

This list of products is given by way of illustration, and is not to be regarded as being in any way limiting.

The invention is now further described with reference to the following non-limiting examples. These examples are for the purpose of illustration only and it is understood that variations and modifications can be made by one skilled in the art.

EXAMPLE 1

6-isopropyl-2,4-dimethylcyclohex-3-en-1-one

1a) Preparation of ethyl 6-isopropyl-2,4-dimethyl-cyclohex-3-ene-1-carboxylate Ethyl (Z)-4-methylpent-2-enoate (28.4 g, 0.2 mol) and (E)-2-methylpenta-1,3-diene (24.6 g, 0.3 mol) were placed in an autoclave. The reactor was sealed and heated to 200° C. for 20 h, the pressure reached 4.5 bar during the course of the reaction. The reaction mixture was distilled over a 10 cm Widmer column to afford ethyl 6-isopropyl-2,4-dimethylcyclohex-3-ene-1-carboxylate (13.47 g, 30% yield) as a colourless oil. Bp 78° C., 0.08 mbar.

1b) Preparation of (6-isopropyl-2,4-dimethylcyclohex-3-en-1-yl)methanol

Ethyl 6-isopropyl-2,4-dimethylcyclohex-3-ene-1-carboxylate (6 g, 26.7 mmol) was dissolved in 30 ml hexane and cooled to −78° C. Diisobutylaluminum hydride (1M, 26.7 mmol) was added drop wise over 30 minutes, keeping the temperature below −65° C.

The mixture was poured onto HCl 2M and extracted with ether to afford (6-isopropyl-2,4-dimethylcyclohex-3-en-1-yl)methanol (4.5 g, 95% yield) as a colorless liquid.

1c) Preparation of 6-isopropyl-2,4-dimethylcyclohex-3-ene-1-carbaldehyde

Pyridinium chlorochromate (8.66 g, 40.2 mmol) and molecular sieve powder 4A (25 g) was suspended in dichloromethane (150 ml) and cooled to 10° C. with an ice bath. Crude (6-isopropyl-2,4-dimethylcyclohex-3-en-1-yl)methanol (4.5 g) was added to the cooled suspension and the mixture was then stirred at room temperature for 3 h. The suspension was diluted with hexane (250 ml) and the solids were filtrated and the solution concentrated in vacuum. The residue was distilled bulb-to-bulb (120° C., 0.5 mbar) to give 6-isopropyl-2,4-dimethylcyclohex-3-ene-1-carbaldehyde (4 g, 83% yield) as a colorless liquid.

1d) Preparation of (E/Z)-4-((6-isopropyl-2,4-dimethylcyclohex-3-en-1-ylidene)methyl)morpholine 6-Isopropyl-2,4-dimethylcyclohex-3-ene-1-carbaldehyde (2.2 g, 12.2 mmol) was placed in a distillation flask and toluene (20 ml) was added. Morpholine (1.3 g, 14.6 mmol) and para-toluene sulfonic acid monohydrate (23 mg, 0.12 mmol) was added and the mixture was refluxed over a Dean-Stark water separator for 2 h. The mixture was concentrated and the residue was purified by chromatography over aluminium oxide with hexane/MtBE 95:5 as the eluent. Pure (E/Z)-4-((6-isopropyl-2,4-dimethylcyclohex-3-en-1-ylidene)methyl)morpholine (1.8 g, 59% yield) was obtained as a colorless liquid.

1e) Preparation of (2R*,6S*)-6-isopropyl-2,4-dimethylcyclohex-3-en-1-one and (2S*,6S*)-6-isopropyl-2,4-dimethylcyclohex-3-en-1-one (E/Z)-4-((6-Isopropyl-2,4-dimethylcyclohex-3-en-1-ylidene)methyl)morpholine (1.47 g, 5.9 mmol) was placed in a reactor and acetonitrile (15 ml) was added. Cu(I)Cl (58 mg, 0.59 mmol) was added and oxygen was bubbled though the stirred mixture for 6 h at room temperature. The reaction mixture was diluted with ether and washed with water and brine. The organic solution was concentrated and the residue was separated by chromatography over $SiO_2$ with hexane/MtBE as the eluent to yield rel-(2R,6S)-6-isopropyl-2,4-dimethylcyclohex-3-en-1-one (100 mg, 10% yield) and rel-(2S,6S)-6-isopropyl-2,4-dimethylcyclohex-3-en-1-one (300 mg, 31% yield) as single diasteromers.

EXAMPLE 2

6-isopropyl-2,4-dimethylcyclohex-3-en-1-ol

2.1 Preparation of rel-(1R,2R,6S)-6-isopropyl-2,4-dimethylcyclohex-3-en-1-ol and rel-(1S,2R,6S)-6-isopropyl-2,4-dimethyloyclohex-3-en-1-ol Aluminum hydride (46 mg, 1.2 mmol) was suspended in THF (5 ml) and the mixture was cooled to −20° C. Compound rel-(2R,6S)-6-isopropyl-2,4-dimethylcyclohex-3-en-1-one (90 mg, 0.5 mmol) was added in portions and the mixture was left to reach room temperature. The reaction mixture was treated with HCl 2M and extracted with ether. The organic layers were combined, washed and concentrated to afford rel-(1R,2R,6S)-6-isopropyl-2,4-dimethylcyclohex-3-en-1-ol and rel-(1S,2R,6S)-6-isopropyl-2,4-dimethylcyclohex-3-en-1-ol (80 mg, 79% yield) as a colorless liquid.

$^1$H-NMR rel-(1R,2R,6S)-6-isopropyl-2,4-dimethylcyclohex-3-en-1-ol (600 MHz, $C_6D_6$): 5.22-5.21 (m, 1H); 3.64-3.69 (m, 1H); 2.25-2.20 (m, 1H); 1.99-1.94 (m, 1H); 1.81 (dd, J=16.9, 4.9, 1H); 1.71-1.63 (m, 1H); 1.66-1.61 (m, 1H); 1.59 (bs, 3H); 1.00 (d, J=7.2, 3H); 0.85 (d, J=7.2, 3H); 0.84 (d, J=6.8, 3H). $^{13}$C-NMR rel-(1R,2R,6S)-6-isopropyl-2,4-dimethylcyclohex-3-en-1-ol (150 MHz, $C_6D_6$): 132.1 (s), 125.4 (d), 70.8 (d), 40.7 (d), 35.2 (d), 29.4 (t), 26.4 (d), 23.5 (q), 20.6 (q), 17.2 (q), 16.4 (q).). MS (EI, tR 9.92 min.): m/z (relative intensity) 168 (5, [M]+•), 107 (60), 106 (26), 91 (15), 83 (73), 82 (100), 71 (28), 67 (48), 55 (16), 43 (20), 41 (25)

$^1$H-NMR rel-(1S,2R,6S)-6-isopropyl-2,4-dimethylcyclohex-3-en-1-ol (600 MHz, $C_6D_6$): 5.20-5.18 (m, 1H); 3.66 (bs, 1H); 2.11-2.06 (m, 1H); 1.79-1.74 (m, 2H); 1.74-1.70 (m, 1H); 1.59 (bs, 3H); 1.16-1.11 (m, 1H); 0.98 (d, J=6.4, 3H); 0.90 (d, J=6.8, 3H); 0.85 (d, J=7.2, 3H). $^{13}$C-NMR rel-(1S,2R,6S)-6-isopropyl-2,4-dimethylcyclohex-3-en-1-ol (150 MHz, $C_6D_6$): 132.8 (s), 123.6 (d), 70.7 (d), 46.7 (d), 39.2 (d), 30.4 (t), 29.1 (d), 23.7 (q), 20.9 (2q), 19.7 (q).

2.2 Preparation of rel-(1S,2R,6R)-6-isopropyl-2,4-dimethylcyclohex-3-en-1-ol and rel-(1R,2R,6R)-6-isopropyl-2,4-dimethylcyclohex-3-en-1-ol Aluminum hydride (80 mg, 2.1 mmol) was suspended in THF (5 ml) and the mixture was cooled to −20° C. Compound (2S*,6S*)-6-isopropyl-2,4-dimethylcyclohex-3-en-1-one (320 mg, 1.9 mmol) was added in portions and the mixture was left to reach room temperature. The reaction mixture was treated with HCl 2M and extracted with ether. The organic layers were combined, washed and concentrated to afford a mixture of rel-(1 S,2R,6R)-6-isopropyl-2,4-dimethylcyclohex-3-en-1-ol and rel-(1R,2R,6R)-6-isopropyl-2,4-dimethylcyclohex-3-en-1-ol (280 mg, 79% yield) as a colorless liquid.

$^1$H-NMR rel-(1S,2R,6R)-6-isopropyl-2,4-dimethylcyclohex-3-en-1-ol (600 MHz, $C_6D_6$): 5.07 (s, 1H); 3.03 (td, J=10.2, 5.3 Hz, 1H); 2.25-2.19 (m, 1H); 2.07-2.01 (m, 1H); 1.70-1.68 (m, 2H); 1.57 (bs, 3H); 1.57-1.53 (m, 1H); 1.06 (d, J=6.8 Hz, 3H); 0.88 (d, J=7.2 Hz, 3H); 0.81 (d, J=6.8 Hz, 3H). $^{13}$C-NMR rel-(1S,2R,6R)-6-isopropyl-2,4-dimethylcyclohex-3-en-1-ol (150 MHz, C$_6$D$_6$): 132.5 (s), 126.0, 75.5, 45.6, 40.5 (4d), 29.7 (t), 25.7 (d), 23.3, 20.7, 19.1, 15.5 (4q). MS (EI, tR 9.92 min.): m/z (relative intensity) 168 (6, [M]+•), 125 (17), 107 (42), 83 (74), 82 (100), 71 (32), 67 (51), 55 (18), 43 (34), 41 (40), 39 (18)

$^1$H-NMR rel-(1R,2R,6R)-6-isopropyl-2,4-dimethylcyclohex-3-en-1-ol (600 MHz, C$_6$D$_6$): 4.96 (s, 1H); 3.72 (bd, J=4.5, 1H); 2.13-2.07 (m, 1H); 1.83 (dd, J=17.7, 6.2, 1H); 1.72-1.65 (m, 1H); 1.68-1.64 (m, 1H); 1.57 (bs, 3H); 1.07-1.03 (m, 1H); 1.00 (d, J=7.2, 3H); 0.97 (d, J=6.4 Hz, 3H); 0.88 (d, J=7.2 Hz, 3H). $^{13}$C-NMR rel-(1R,2R,6R)-6-isopropyl-2,4-dimethylcyclohex-3-en-1-ol (150 MHz, C$_6$D$_6$): 133.4 (s), 123.8 (d), 69.1 (d), 46.4 (d), 37.0 (d), 30.4 (t), 29.5 (d), 23.2 (q), 20.8 (q), 20.7 (q), 17.4 (q). MS (EI, tR 9.92 min.): m/z (relative intensity) 168 (8, [M]+•), 125 (22), 107 (52), 106 (18), 83 (73), 82 (100), 71 (28), 67 (48), 55 (16), 43 (21), 41 (27)

EXAMPLE 3

Preparation of 2,4,7-trimethyloctan-1-ol

An autoclave was charged with 2,4,7-trimethyloct-6-en-1-ol (15.0 g, 88 mmol) and 20% palladium on carbon (150 mg, 1% [w]). The autoclave was flushed with nitrogen and then pressurized to 40 bar with hydrogen. The hydrogenation was performed at 150° C. for 20 hours. After cooling to room temperature, the catalyst was removed by filtration and the product was purified by flash distillation (b.p. 85° C., 0.23 mbar) to afford 2 (11.5 g, 76% yield).

$^1$H-NMR (400 MHz, CDCl$_3$) mixture of diastereomers ratio 1/1.3:3.59-3.34 (m, 4H); 1.61-1.81 (m, 4H); 1.56-1.39 (m, 4H); 1.33-1.04 (m, 10H); 0.97-0.80 (m, 26H). $^{13}$C-NMR (100 MHz, CDCl$_3$) mixture of diastereomers ratio 1/1.3: 69.0, 68.0, 41.1, 40.7, 36.3, 36.2, 35.7, 34.3 (8t); 33.2, 33.1, 30.3, 30.2, 28.3 (6d); 22.9, 22.8, 22.6, 22.5, 20.4, 19.4, 17.3, 16.3.

EXAMPLE 4

Preparation of bis((3-methylbut-2-en-1-yl)oxy)methane

A three neck flask, equipped with a Dean-Stark water separator, was charged with 3-methylbut-2-en-1-ol (40.0 g, 464 mmol), formaldehyde (17.43 g, 232 mmol, 40% in water), triethylamine hydrochloride (1.5 g, 11 mmol) and toluene (100 ml). The mixture was refluxed for 20 hours. The reaction mixture was cooled to room temperature and diluted with methyl tert.-butyl ether (100 ml). The organic solution was washed twice with water (50 ml) and with brine (50 ml), then dried over MgSO$_4$ and concentrated. The crude product was purified by column chromatography and bulb-to-bulb distillation to give bis((3-methylbut-2-en-1-yl)oxy)methane (I) (6.0 g, 33 mmol, 14% yield).

$^1$H-NMR (300 MHz, CDCl$_3$): 5.44-5.31 (m, 2H); 4.69 (s, 2H); 4.07 (br d, J=6.99 Hz, 4H); 1.76 (s, 6H); 1.70 (s, 6H). $^{13}$C-NMR (75 MHz, CDCl$_3$): 137.4 (2s); 120.6 (2d); 93.7 (t); 63.7 (2t); 25.7 (2q); 17.9 (2q).

EXAMPLE 5

Perfuming Composition (Unisex) to be Applied @ 1% in Shower Gel

| Ingredient | parts per weight | |
|---|---|---|
| Dipropylene Glycol (DPG) | 27 | |
| Hexyl acetate | 17 | |
| Hexyl salicyclate | 580 | 570 |
| Javanol ® | 1 | |
| Lilial (3-(4-(tert-butyl)phenyl)-2-methylpropanal) | 200 | |
| Manzanate (ethyl 2-methylpentanoate) | 3 | |
| Methyl Laitone (8-methyl-1-oxaspiro[4.5]decan-2-one ) @ 10% TEC | 100 | |
| Methyl Pamplemousse (6,6-dimethoxy-2,5,5-trimethylhex-2-ene) | 20 | |
| Milk Lactone (decenoic acid) | 20 | |
| Nerolione (1-(3-methylbenzofuran-2-yl)ethan-1-one) @ 10% TEC | 10 | |
| Paradisamined (2-ethyl-N-methyl-N-(m-tolyl)butanamide) | 20 | |
| Pomarose (5,6,7-trimethylocta-2,5-dien-4-one) | 1 | |
| Zinarine (2-(2,4-dimethylcyclohexyl)pyridine) | 1 | |
| 6-isopropyl-2,4-dimethylcyclohex-3-en-1-ol | 0 | 10 |
| TOTAL | 1000 | 1000 |

The accord above is a milky fruity accord to illustrate a juicy, over ripe fig with a clear milky facet. The addition of 10 parts of 6-isopropyl-2,4-dimethylcyclohex-3-en-1-ol results in an accord with more lift, with a natural fig leaf facet.

The invention claimed is:
1. A compound of formula (I)

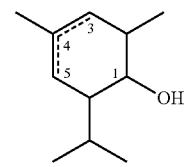

(I)

wherein the dotted line between C-3 to C-4 together with the carbon-carbon bond forms a single bond and the dotted line between C-4 and C-5 together with the carbon-carbon bond forms a double bond; or
wherein the dotted line between C-3 to C-4 together with the carbon-carbon bond forms a double bond and the dotted line between C-4 and C-5 together with the carbon-carbon bond forms a single bond.

2. The compound according to claim 1 selected from 6-isopropyl-2,4-dimethylcyclohex-3-en-1-ol, 6-isopropyl-2,4-dimethylcyclohex-4-en-1-ol, and mixtures thereof.

3. A method comprising utilizing a compound of formula (I)

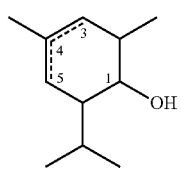

(I)

wherein the dotted line between C-3 to C-4 together with the carbon-carbon bond forms a single bond and the dotted line between C-4 and C-5 together with the carbon-carbon bond forms a double bond; or wherein the dotted line between C-3 to C-4 together with the carbon-carbon bond forms a double bond and the dotted line between C-4 and C-5 together with the carbon-carbon bond forms a single bond;

as fragrance, alone or in combination with a base material as a fragrance composition; the method comprising mixing the compound of formula (I) or fragrance composition directly, entrapped with an entrapment material, or bonded to a substrate adapted to release the compound upon application of an external stimulus, with a consumer product base.

4. A fragranced article comprising as odorant a compound of formula (I) as defined in claim 1, or a mixture thereof, and a consumer product base.

5. The fragranced article according to claim 4 wherein the consumer product base is selected from fine perfumery, household products, laundry products, fabric care products, body care products, cosmetic products and air care products.

6. A method of improving, enhancing or modifying a consumer product base comprising adding to the consumer product base an olfactory acceptable amount of a compound of formula (I) as defined in claim 1.

7. A fragrance composition comprising a compound of formula (I) as defined in claim 1 and at least one other compound selected from the group consisting of 2,4,7-trimethyloct-6-en-1-ol, 2,4,7-trimethylocta-2, 6-di en-1-ol, 2,4,7-trimethylocta-3, 6-dien-1-ol, 2,4,7-trimethyloctan-1-ol, and bis((3-methylbut-2-en-1-yl)oxy)methane.

8. The fragrance composition according to claim 7 wherein the compound of formula (I) is 6-isopropyl-2,4-dimethylcyclohex-3-en-1-ol.

\* \* \* \* \*